(12) United States Patent
Pikkula et al.

(10) Patent No.: US 10,345,680 B2
(45) Date of Patent: Jul. 9, 2019

(54) OPTICAL FILTERING ATTACHMENT

(71) Applicant: Forward Science Technologies, LLC, Stafford, TX (US)

(72) Inventors: Brian Pikkula, Sugar Land, TX (US); Robert Whitman, Houston, TX (US)

(73) Assignee: FORWARD SCIENCE TECHNOLOGIES, LLC, Stafford, TX (US)

(*) Notice: Subject to any disclaimer, the term of this patent is extended or adjusted under 35 U.S.C. 154(b) by 303 days.

(21) Appl. No.: 14/284,245

(22) Filed: May 21, 2014

(65) Prior Publication Data

US 2015/0070480 A1    Mar. 12, 2015

Related U.S. Application Data

(63) Continuation-in-part of application No. PCT/US2013/048159, filed on Jun. 27, 2013.

(60) Provisional application No. 61/825,712, filed on May 21, 2013.

(51) Int. Cl.

| G03B 17/56 | (2006.01) |
| G06T 7/00 | (2017.01) |
| H04M 1/725 | (2006.01) |
| G03B 11/00 | (2006.01) |
| H04N 7/18 | (2006.01) |
| G03B 15/02 | (2006.01) |

(Continued)

(52) U.S. Cl.
CPC ............ *G03B 11/00* (2013.01); *A61B 5/0088* (2013.01); *A61B 5/4887* (2013.01); *A61B 5/6898* (2013.01); *G03B 15/02* (2013.01); *H04N 5/2254* (2013.01); *A61B 5/682* (2013.01); *H04N 7/185* (2013.01)

(58) Field of Classification Search
CPC ...... G03B 11/00; G03B 15/02; H04N 5/2254; H04N 7/185; A61B 5/6898; A61B 5/0088; A61B 5/4887; A61B 5/682
See application file for complete search history.

(56) References Cited

U.S. PATENT DOCUMENTS

| 6,494,572 B1* | 12/2002 | Sinoway ................ G02C 7/086 351/47 |
| 7,674,002 B1* | 3/2010 | Wang ...................... A45B 3/02 248/231.51 |
| 7,802,898 B1 | 9/2010 | Gregory et al. |

(Continued)

FOREIGN PATENT DOCUMENTS

| EP | 1693021 A1 | 8/2005 |
| WO | 2009097154 A1 | 8/2009 |

*Primary Examiner* — Mohammad J Rahman
(74) *Attorney, Agent, or Firm* — Leydig, Voit & Mayer, Ltd.

(57) ABSTRACT

The present disclosure introduces an optical component attachable to a mobile communications device and operable to spectrally filter images taken by a camera of the mobile device. Systems introduced herein include the optical component, the mobile device, and an illumination source for directing light at a specific wavelength/intensity into a human mouth, such that images taken by the camera record human mouth tissue responses to the light for cancer screening purposes. Such cancer screening may also utilize a database of other response images from other patients, which may be transmitted to the database by the mobile device and/or other mobile devices.

20 Claims, 9 Drawing Sheets

(51) Int. Cl.
*A61B 5/00* (2006.01)
*H04N 5/225* (2006.01)

(56) References Cited

U.S. PATENT DOCUMENTS

| | | | |
|---|---|---|---|
| 7,967,513 B2* | 6/2011 | Zhang | G02B 7/182 |
| | | | 396/351 |
| 8,073,324 B2* | 12/2011 | Tsai | H01F 7/0247 |
| | | | 359/827 |
| 8,337,201 B1 | 12/2012 | Mace | |
| 8,755,850 B2* | 6/2014 | Kang | G03B 17/14 |
| | | | 455/557 |
| 8,786,689 B1* | 7/2014 | Liu | A61B 1/00034 |
| | | | 348/68 |
| 8,891,187 B2* | 11/2014 | O'Neill | G02B 7/14 |
| | | | 359/819 |
| 9,007,522 B1* | 4/2015 | O'Neill | G02B 7/14 |
| | | | 348/375 |
| 9,195,023 B2* | 11/2015 | O'Neill | G02B 7/02 |
| 9,294,660 B2* | 3/2016 | O'Neill | H04N 5/2254 |
| 9,423,671 B2* | 8/2016 | O'Neill | G03B 15/06 |
| 9,454,066 B2* | 9/2016 | O'Neill | G03B 17/565 |
| 9,571,151 B2* | 2/2017 | O'Neill | H04B 1/3888 |
| 9,661,200 B2* | 5/2017 | O'Neill | H04N 5/2254 |
| 2004/0218081 A1* | 11/2004 | Lohr | G02B 7/00 |
| | | | 348/335 |
| 2005/0080343 A1 | 4/2005 | Richards-Kortum et al. | |
| 2007/0196090 A1* | 8/2007 | Kubo | G03B 17/02 |
| | | | 396/71 |
| 2008/0291394 A1* | 11/2008 | Ishak | G02C 7/12 |
| | | | 351/159.6 |
| 2009/0143099 A1* | 6/2009 | Kang | G03B 17/14 |
| | | | 455/556.1 |
| 2009/0181729 A1* | 7/2009 | Griffin, Jr. | H04N 5/2254 |
| | | | 455/575.1 |
| 2009/0268157 A1* | 10/2009 | Krieg-Kowald | G02B 5/223 |
| | | | 351/159.63 |
| 2009/0323344 A1 | 12/2009 | Crawford et al. | |
| 2010/0142938 A1* | 6/2010 | Zhang | G02B 7/182 |
| | | | 396/384 |
| 2010/0254149 A1 | 10/2010 | Gill | |
| 2010/0328420 A1* | 12/2010 | Roman | H04N 5/2251 |
| | | | 348/14.08 |
| 2011/0117025 A1* | 5/2011 | Dacosta | A61B 5/0059 |
| | | | 424/9.6 |
| 2011/0143583 A1* | 6/2011 | Zilmer | H04M 1/04 |
| | | | 439/529 |
| 2011/0164411 A1* | 7/2011 | Sparing | F21L 4/00 |
| | | | 362/197 |
| 2012/0226117 A1* | 9/2012 | Lamego | A61B 5/14532 |
| | | | 600/316 |
| 2012/0243200 A1* | 9/2012 | Sutton | G03B 15/02 |
| | | | 362/11 |
| 2013/0209954 A1* | 8/2013 | Prakash | A61B 1/0005 |
| | | | 433/29 |
| 2013/0217449 A1* | 8/2013 | Lehmann | H04M 1/05 |
| | | | 455/575.2 |
| 2014/0043436 A1* | 2/2014 | Bell | H04N 13/0203 |
| | | | 348/46 |
| 2014/0060570 A1* | 3/2014 | Tsai | A45D 8/24 |
| | | | 132/277 |
| 2014/0071547 A1* | 3/2014 | O'Neill | G02B 7/02 |
| | | | 359/827 |
| 2014/0073880 A1* | 3/2014 | Boucher | A61B 1/227 |
| | | | 600/301 |
| 2014/0356864 A1* | 12/2014 | Khan | G01N 21/25 |
| | | | 435/5 |
| 2015/0087926 A1* | 3/2015 | Raz | A61B 5/0013 |
| | | | 600/301 |

\* cited by examiner

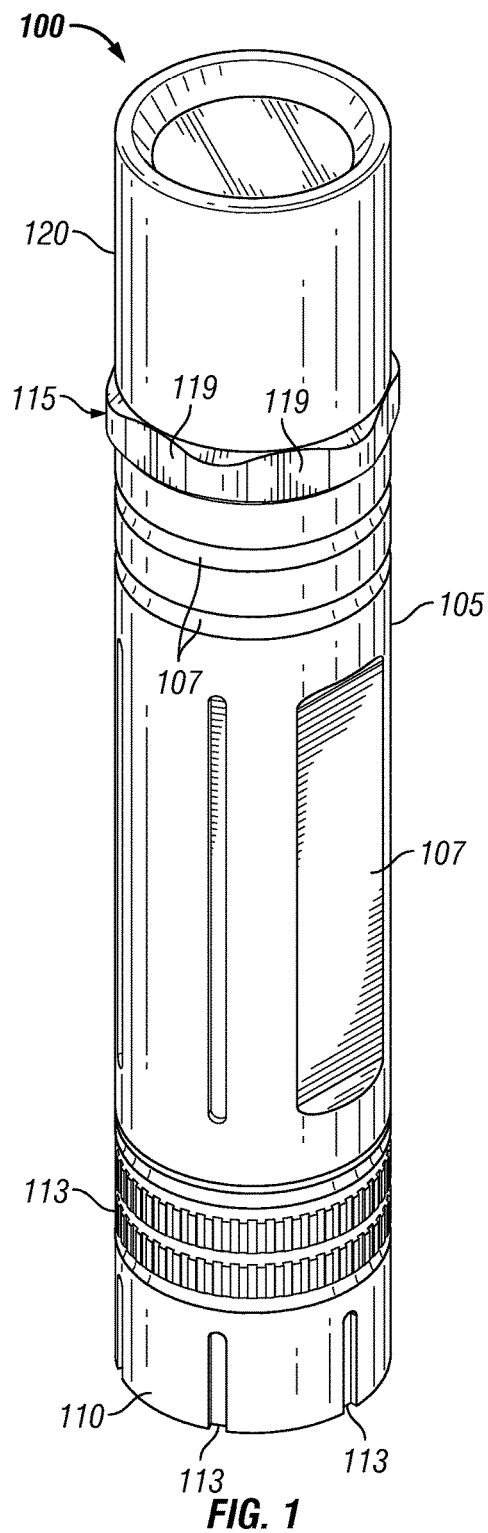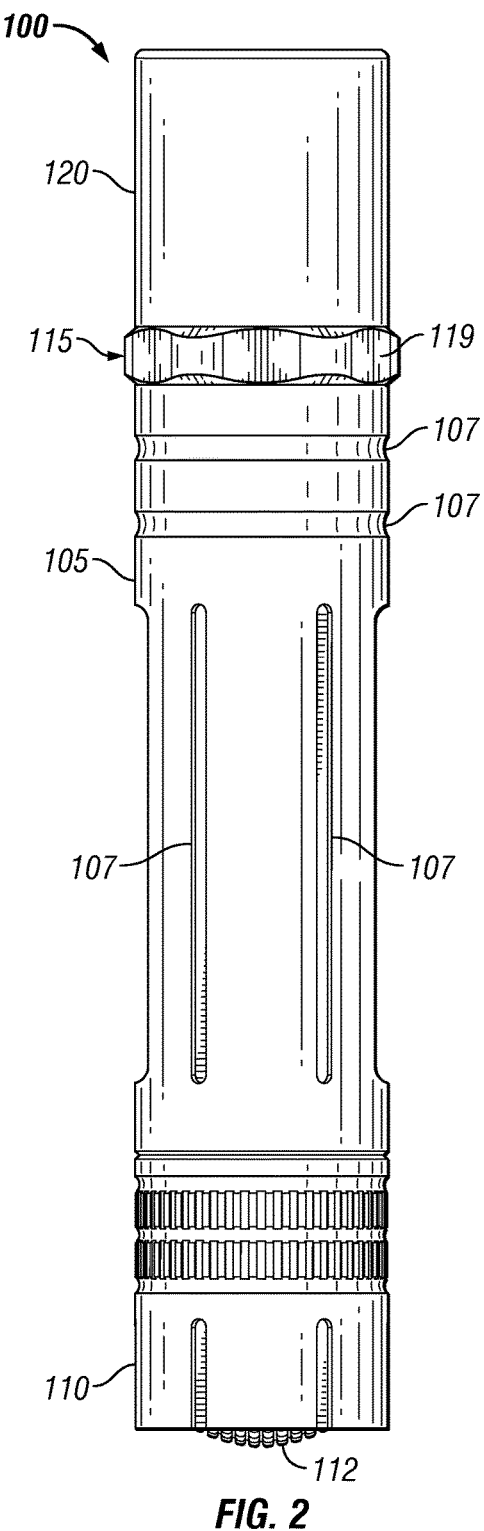

OPTICAL FILTERING ATTACHMENT

CROSS-REFERENCE TO RELATED APPLICATIONS

The present application is a continuation-in-part of International patent application No. PCT/US2013/048159, entitled "Oral Examination," filed Jun. 27, 2013, the entire disclosure of which is hereby incorporated herein by reference.

The present application also claims the benefit of and priority to U.S. Provisional Patent Application No. 61/825,712, entitled "Optical Filtering Attachment," filed May 21, 2013, the entire disclosure of which is hereby incorporated herein by reference.

BACKGROUND OF THE DISCLOSURE

In oral cancer screening, diagnoses can be limited by lack of comprehensive and accurate image libraries to assist in assessing clinical images of abnormal tissue. Current methods of imaging such tissue involve the use of Digital Single Lens Reflex cameras (DSLRs), which may be challenging to use for those without extensive photography skills, have inadequate depth of field for imaging abnormal tissue, and may be limited in use to specific or qualified personnel. Existing image libraries are online only and do not provide the care giver with information to assist in making a clinical decision.

BRIEF DESCRIPTION OF THE DRAWINGS

The present disclosure is best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

FIG. 1 is a perspective view of at least a portion of apparatus according to one or more aspects of the present disclosure.

FIG. 2 is a side view of the apparatus shown in FIG. 1.

DETAILED DESCRIPTION

Figure 3:
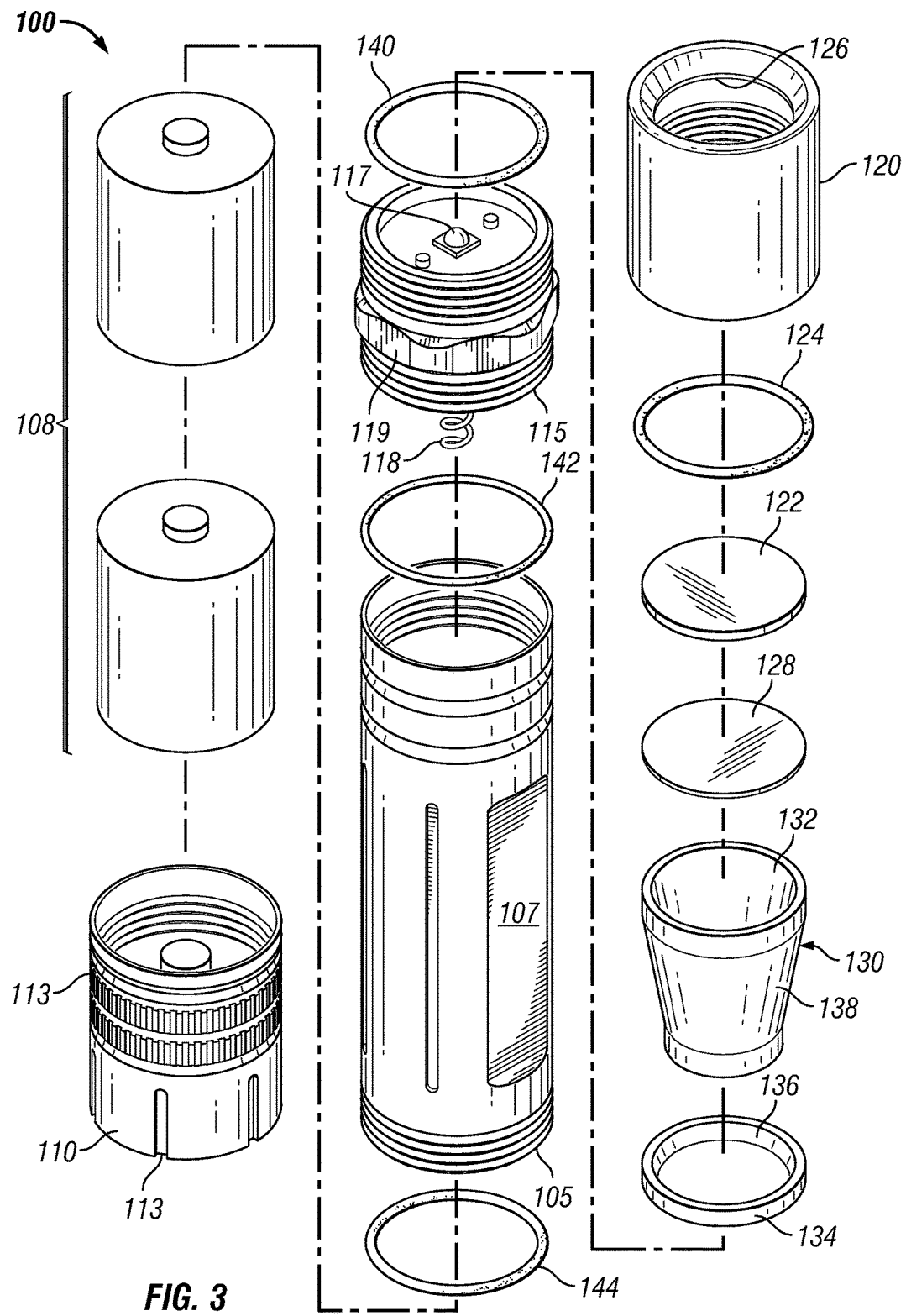
FIG. 3 is an exploded view of the apparatus shown in FIGS. 1 and 2.

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed. Additionally, the term "lens" as used herein may mean an optical component that diverges or converges an optical beam as well an optical component that does not converge or diverge an optical beam.

FIGS. 1-3 are perspective, front, and exploded views, respectively, of at least a portion of apparatus 100 according to one or more aspects of the present disclosure. Referring to FIGS. 1-3 collectively, the apparatus 100 may comprise a housing 105, a first end cap 110, an interstitial member 115, and a second end cap 120, all coupled end-to-end in the order listed, as shown in FIG. 1. However, the housing 105, the first end cap 110, the interstitial member 115, and the second end cap 120, a subset thereof, and/or additional components may be coupled or otherwise interconnected in a manner other than as shown in FIG. 1, and such implementations are also within the scope of the present disclosure.

The housing 105 may be or comprise a partially or substantially cylindrical tube. One or more recessed and/or protruding features 107 may be formed integrally with or otherwise coupled to the housing 105. Such features may extend axially along at least a portion of the housing 105, circumferentially around at least a portion of the housing 105, or a combination thereof, which may assist with securely gripping the apparatus 100. Opposing ends of the housing 105 may be threaded and/or otherwise configured to couple with the first end cap 110 and the interstitial member 115. For example, in the implementation depicted in FIGS. 1 and 2, the housing 105 comprises external threads to couple with the first end cap 110 and internal threads to couple with the interstitial member 115. Of course, other means for coupling the first end cap 110 and/or the interstitial member 115 with the housing 105 are also within the scope of the present disclosure. The housing 105 may comprise metal, plastic, and/or other substantially rigid materials, perhaps including materials that may be disinfected and/or sterilized by conventional and/or future-developed processes, such as for use in a dental office and/or other medical environments.

The housing 105 contains an electrical energy source 108, which in the implementation depicted in FIG. 3 comprises two batteries. The batteries may be alkaline, NiCd, NiMH, NiZn, lithium, lithium ion, silver-oxide, galvanic, electrolytic, wet cells, dry cells, and/or other types of batteries. For example, the batteries may be CR123A batteries, such as those available from ENERGIZER and DURACELL. In other implementations, the electrical energy source 108 may comprise components other than batteries, such as circuitry for connection to a facility electrical system, or a mechanically powered energy source that generates electrical power by shaking, squeezing, winding, and/or otherwise moving the housing 105 and/or another component of the apparatus 100.

The first end cap 110 may comprise a control 112 (FIG. 2) operable to electrically connect the electrical energy source 108 to other electronic components of the apparatus 100 described below. For example, the control 112 may comprise a push button control, a rotatable knob, and/or a switch, although other control types are also within the scope of the present disclosure. The first end cap 110 may also comprise one or more patterned, recessed, and/or protruding portions 113, such as may assist in removing and/or assembling the first end cap 110 to the housing 105.

The interstitial member 115 comprises a light source 117 that may be selectively energized by the electrical energy source 108 via operation of the control 112. The light source 117 may comprise one or more light emitting diodes (LEDs). For example, the light source 117 may be an LED that emits in the blue and/or violet sections of the visible spectrum, such as at a wavelength of about 450 nm or otherwise in the range of about 350 nm to about 500 nm. Intensity of the light energy emitted by the light source 117 may be about 500 mW or otherwise in the range of about 75 mW to about 2000 mW. However, other means may also or alternatively be utilized for the light source 117 within the scope of the present disclosure.

The interstitial member 115 may also comprise one or more components forming an electrical path between the electrical energy source 108 and the light source 117. For example, such an electrical path may comprise a spring and/or other member 118 extending from the interstitial member 115 to the electrical energy source 108, and/or various electronic components and/or circuitry, perhaps including one or more LED drivers, resistors, capacitors, transformers, voltage cut-off coils, low-pass filters, high-pass filters, band-stop filters, band-pass filters, integrated circuits, and/or others (not shown).

The second end cap 120 comprises an optical filtering component 122 that is in substantial optical alignment with the light source 117 and/or light emitted therefrom. The optical filtering component 122 may be or comprise a low-pass filter, a high-pass filter, a band-stop filter, and/or a band-pass filter, although other filters are also within the scope of the present disclosure. An O-ring 124 may be positioned between the optical filtering component 122 and an inside lip 126 of the second end cap 120, such as to create a seal prevent fluid from entering the apparatus via the interface between the optical filtering component 122 and the inside lip 126. The second end cap 120 may further comprise a diffuser 128 positioned to diffuse the light emitted by the light source 117 before the light is incident upon the optical filter component 122, such as to reduce the sharpness of the edges of the beam of light emitted by the light source 117. The optical filtering component 122 and/or the diffuser 128 may comprise glass, plastic, and/or other materials providing the appropriate optical characteristics.

A reflector 130 may also be positioned at least partially within the second end cap 120 in substantial optical alignment between the light source 117 and the optical filtering component 122. An internal surface 132 of the reflector 130 may be polished, painted, and/or otherwise configured to centrally focus the light energy emitted by the light source 117. The reflector 130 may comprise metal, plastic, and/or any other suitable material, and may be secured within the second end cap 120 by a retaining ring 134. For example, the retaining ring 134 may have an internal sloped surface 136 configured to cooperate with an external sloped surface 138 of the reflector 130, such that threading and/or otherwise assembling the retaining ring 134 into corresponding internal threads and/or other features of the second end cap 120 urges the sloped surfaces 136 and 138 together, thus urging the reflector 130 towards the internal lip 126 of the second end cap 120 and compressing the O-ring 124 to form the desired seal. The cooperating sloped surfaces 136 and 138 may also center the reflector 130 relative to a longitudinal axis of the second end cap 120 and/or otherwise aid in optically aligning the reflector 130 between the light source 117 and the optical filtering component 122.

At least a portion of an exterior of at least one of the housing 105, the first end cap 110, the interstitial member 115, and the second end cap 120 may have a cross-sectional shape that is not substantially circular. For example, as shown in the implementation depicted in FIGS. 1-3, a portion of the external surface of the interstitial member 115 may comprise one or more flats 119, such as may aid in preventing the apparatus 100 from rolling when resting on a substantially horizontal surface. However, one or more of the housing 105, the first end cap 110, and the second end cap 120 may alternatively or additionally comprise one or more such features. In addition to the flats 119 shown in FIGS. 1-3, or as an alternative thereto, the cross-sectional shape of the housing 105, the first end cap 110, the interstitial member 115, and/or the second end cap 120 may have at least a portion that is square, rectangular, elliptical, and/or otherwise substantially non-circular. Such features may be integrally formed with one or more corresponding components of the apparatus 100, and/or may be discrete members that are coupled to one or more of such components.

At least a portion of an exterior surface of one or more of the housing 105, the first end cap 110, the interstitial member 115, and the second end cap 120 may also comprise a material that provides substantial gripping force, such as rubber and/or other pliable materials. Such gripping features may be the same as the anti-roll features described above.

As described above, the interface between the optical filtering component 122 and the internal lip 126 of the second end cap 120 may be sealed and/or otherwise made waterproof by compression of the interposing O-ring 124. The interconnection of the other components of the apparatus 100 may also comprise similar sealing and/or other features. For example, the interface between the second end cap 120 and the interstitial member 115 may be sealed and/or otherwise made waterproof by compression of a similar O-ring 140 and/or other means. Similarly, the interface between the interstitial member 115 and the housing 105 may be sealed and/or otherwise made waterproof by compression of a similar O-ring 142 and/or other means. The interface between the housing 105 and the first end cap 110 may also be sealed and/or otherwise made waterproof by compression of a similar O-ring 144 and/or other means. The O-rings 124, 140, 142, and 144 and/or additional or alternative sealing means may seal and/or otherwise make the apparatus 100 waterproof such that, once the apparatus 100 is assembled, no fluids may enter any internal cavity of the apparatus 100.

Having described various details and alternatives with respect to the apparatus 100 shown in FIGS. 1-3, operation of the apparatus 100 will now be described with reference to FIG. 4, which is a schematic view of a dentist, hygienist, and/or other medical personnel 410 utilizing the apparatus 100 to perform oral examination of a patient 420, such as to identify oral cancer, pre-cancer, and/or other oral mucosal abnormalities. The apparatus 100 may be made commercially available as part of a kit that also contains one or more eyewear devices 430 to be worn by the medical personnel 410 and, perhaps, the patient 420 during the oral examination procedure.

The eyewear devices 430 may comprise an optical filtering component to be utilized in conjunction with the optical filtering component 122 shown in FIGS. 1-3. For example, the lenses of the eyewear device(s) 430 may comprise a low-pass filter, and the optical filtering component 122 of the apparatus 100 may comprise a high-pass filter. Alternatively, the lenses of the eyewear device(s) 430 may comprise a high-pass filter, and the optical filtering component of the apparatus 100 may comprise a low-pass filter. Similarly, the lenses of the eyewear device(s) 430 and the optical filtering component of the apparatus 100 may comprise different ones of a low-pass filter, a high-pass filter, a band-stop filter, a band-pass filter, and/or other types of filters. The combination of filters may be operable in conjunction with the light emitted by the apparatus 100 to detect cancerous and/or pre-cancerous regions and/or other mucosal abnormalities of the oral cavity of the patient 420. For example, the two filters may remove all (or substantially all) light emitted by the apparatus 100, including that which may reflect off of surfaces of the oral cavity of the patient 420, such that only the light resulting from fluorescence of the mucosal abnormalities remains visible to the medical personnel 410 wearing the eyewear device 430. Alternatively, the two filters and the light emitted by the apparatus 100 may work in conjunction to dim any light other than the fluorescence emanating from the mucosal abnormalities. The patient 420 may also wear an eyewear device 430 to, for example, block at least a portion of the light emitted by the apparatus 100 from entering their eyes.

Figure 4:
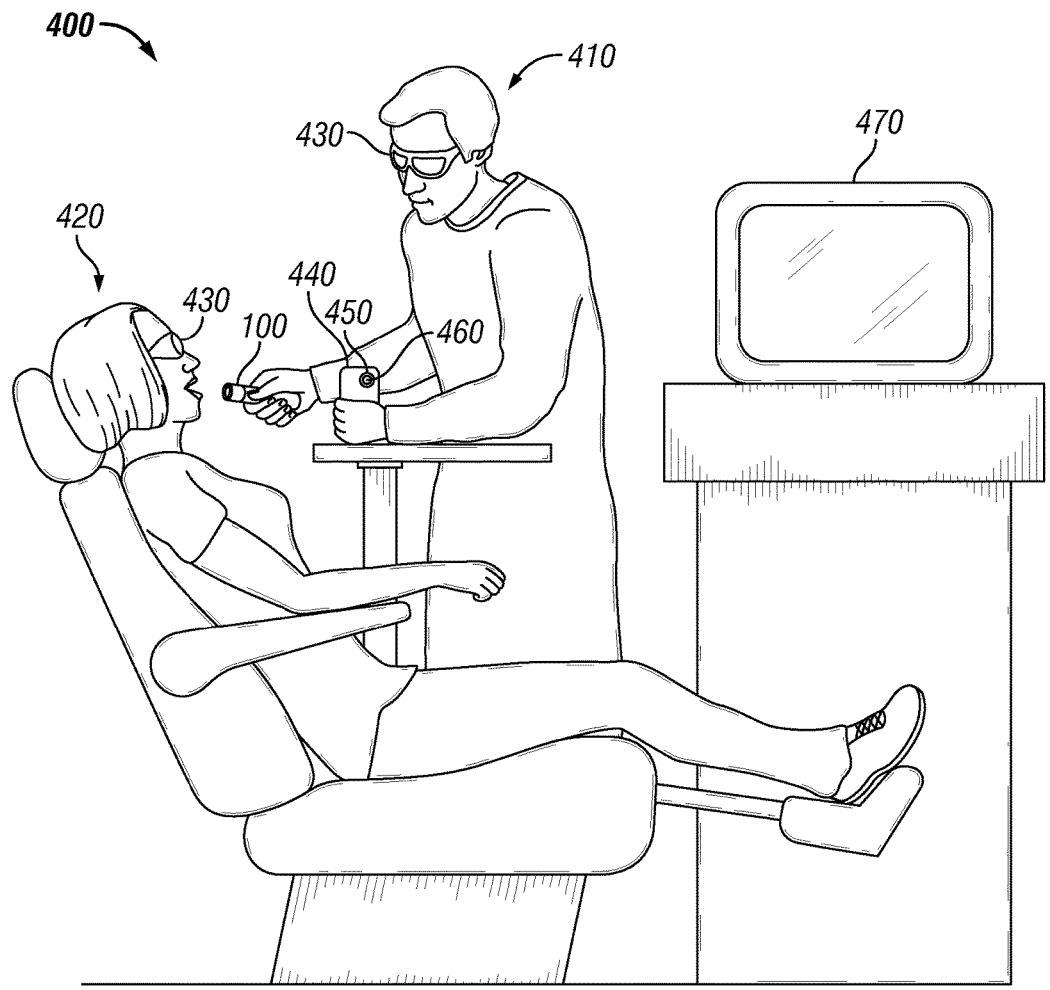
FIG. 4 is a schematic view of at least a portion of apparatus according to one or more aspects of the present disclosure.
Figure 5:
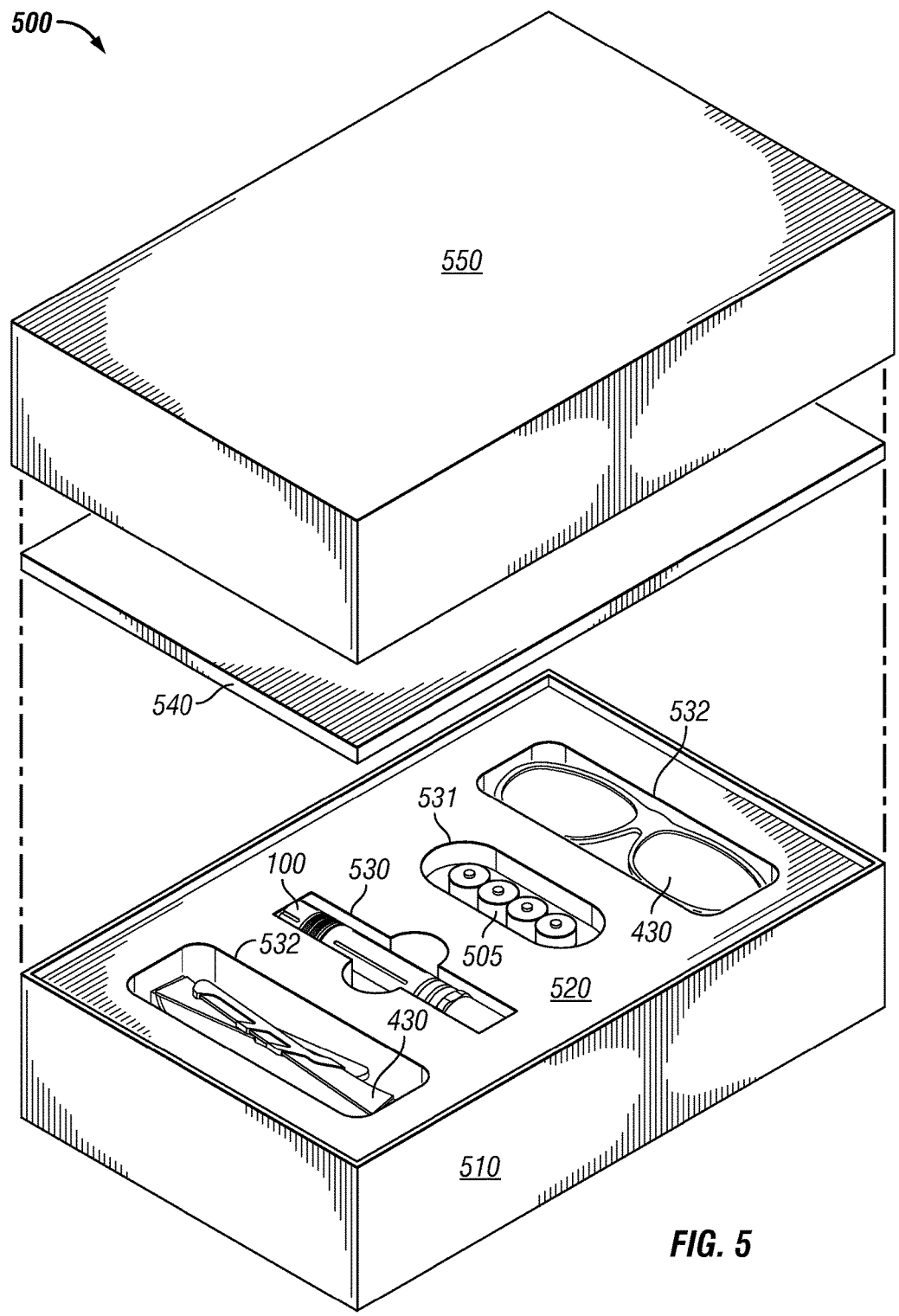
FIG. 5 is a schematic view of at least a portion of a kit according to one or more aspects of the present disclosure.

FIG. 5 is a schematic view of a kit 500 according to one or more aspects of the present disclosure. The kit 500 may comprise one or more instances of the apparatus 100 shown in FIGS. 1-4 and one or more of the eyewear devices 430 shown in FIG. 4. In the example implementation depicted in FIG. 5, the kit 500 also comprises spare batteries and/or other components 505 of the electrical energy source 108 shown in FIG. 2. The kit 500 may also or instead comprise other components described below and/or shown in subsequent figures, perhaps including apparatus shown in one or more of FIGS. 7-10.

The components of the kit 500 may be packaged in one or more boxes and/or other containers 510, perhaps within an insert 520 having recessed features 530-532 sized to receive corresponding components of the kit 500, such as may aid in protecting the components of the kit from mechanical shocks and/or other forces that may be experienced during handling, shipping, and/or otherwise. For example, the insert 520 may comprise foam and/or other shock-absorbing materials, and may have a first feature 530 sized to receive the apparatus 100 in a manner substantially preventing movement of the apparatus 100 within the container 510. Similarly, a second feature 531 may be sized to receive a predetermined number of batteries (four being shown in FIG. 5), and third features 532 may each be sized to receive one of the eyewear devices 430. Each of the second and third features 531 and 532 may also substantially prevent movement of the batteries and eyewear devices within the container 510. The kit 500 may also comprise an additional insert 540 covering the components of the kit 500 before a cover 550 is assembled to the container 510.

Figure 6:
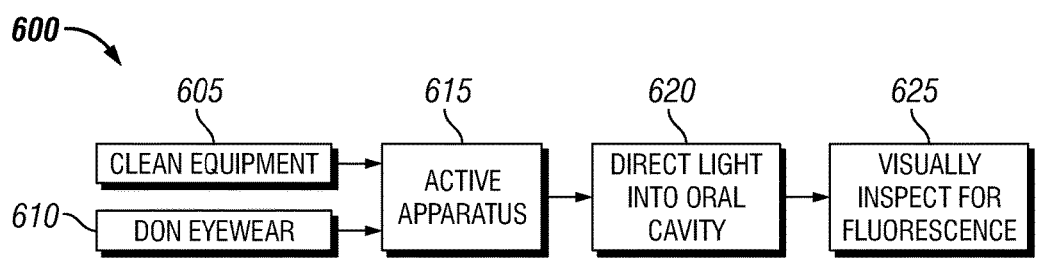
FIG. 6 is a flow-chart diagram of at least a portion of a method according to one or more aspects of the present disclosure.

FIG. 6 is a flow-chart diagram of at least a portion of a method 600 according to one or more aspects of the present disclosure. The method 600 may utilize at least a portion of the apparatus described above, such as the apparatus 100 shown in FIGS. 1-5 and/or the eyewear devices 430 shown in FIGS. 4 and 5. The method 600 may also utilize other components described below and/or shown in subsequent figures, perhaps including apparatus shown in one or more of FIGS. 7-10.

The method 600 may comprise cleaning (605) one or more pieces of equipment to be utilized during the method 600. For example, this may entail cleaning the apparatus 100 shown in FIGS. 1-5 and/or the eyewear devices 430 shown in FIGS. 4 and 5. Such cleaning may comprise disinfecting and/or sterilizing the equipment. For example, the apparatus 100 shown in FIGS. 1-5 and/or the eyewear devices 430 shown in FIGS. 4 and 5 may be submersed in a sanitizing solution, such as CAVICIDE (available from UNIMED), MAXICIDE (available from HENRY SCHEIN, INC.), and/or isopropyl alcohol, although other disinfecting and/or sanitizing products may also or alternatively be utilized. Disinfecting and/or sterilizing the equipment may also or alternatively comprise autoclaving and/or thoroughly wiping the equipment with a sanitizing fabric, paper, and/or other wipe.

The method 600 may also comprise donning (610) an eyewear device, such as the eyewear device 430 shown in FIGS. 4 and 5. This may entail one or both of the medical personnel and the patient donning the eyewear.

The light-emitting apparatus 100 shown in FIGS. 1-5 may then be activated (615). As described above, such activation may be via operation of a control of the apparatus, such as a push-button, rotating knob, switch, and/or other control. After activating the apparatus, the medical personnel may then direct (620) light emitted by the activated apparatus into the oral cavity of the patient. For example, the medical personnel may position the light emitting apparatus proximate the patient's oral cavity and orient the apparatus such that all or a substantial portion of the emitted light enters the patient's oral cavity. However, this procedure does not include inserting the light-emitting apparatus into the patient's oral cavity. Thereafter, the medical personnel may visually inspect (625) for fluorescence emitted by cancerous areas, pre-cancerous areas, and/or other mucosal abnormalities of the patient's oral cavity by looking through the eyewear.

The order of the above-described portions of the method 600 may vary within the scope of the present disclosure. For example, the equipment cleaning may be performed prior to activating the light-emitting apparatus and/or after directing the emitted light into the patient's oral cavity. It is also noteworthy that the method 600 does not include utilizing any type of disposable that is discarded after each iteration of the method. For example, the method 600 does not include assembling a rigid or flexible plastic sleeve over the light-emitting apparatus, and thus does not include disposing of such sleeves.

Returning to the example implementation of the screening system 400 shown in FIG. 4, the medical personnel 410 may utilize a camera 450 of a mobile communications device 440 to take images of the oral cavity of the patient 420. An optical component 460 may be operable to spectrally filter images taken by the camera 450 of the mobile communications device 440. The optical component 460 may be or comprise a high-pass, a low-pass filter, a band-stop filter, and/or a band-pass filter, although other types of light filters are also within the scope of the present disclosure. The optical component 460 may remove all (or substantially all) light emitted by the illumination source 100, including that which may reflect off of surfaces of the oral cavity of the patient 420, such that only a fluorescent signal from the tissue may remain visible to the camera 440. Thus, the optical component 460 may be at least functionally similar to the eyewear 430 donned by the medical personnel 410.

The optical component 460 may be made commercially available as part of a kit that also contains the illumination source 100, such as the kit 500 shown in FIG. 5. The kit may also comprise one or more eyewear devices 430 to be worn by the medical personnel 410 and/or the patient 420 during the oral screening procedure. The eyewear devices 430 may be utilized in conjunction with the illumination source 100.

The system 400 may also comprise a computer 470. The computer 470 may be operable to receive spectrally filtered image data from the mobile communications device 440 and/or other computing devices, such as those shown in subsequent figures and described below. The computer 470 may also be operable to store the image data, and perhaps to transmit the image data, such as to another mobile communications device, computer, and/or other computing device.

The mobile communications device 440 is operable to obtain, store, and transmit image data obtained utilizing the camera 450. For example, the mobile communications device 440 may be operable to transmit the image data to at least one of another mobile communications device, the computer 470, and a database. Such database may be embodied or implemented in the computer 470 or another computing device. The database, or a computing device comprising the database, may be operable to be accessed by the mobile communications device 440, another mobile communications device (such as may be remotely located), the computer 470, another computer (such as may be remotely located), and/or another database (such as may be remotely located). The database or a computing device comprising the database may also or instead be operable to transmit at least a portion of the image data to the mobile communications device 440, another mobile communications device (such as may be remotely located), the computer 470, another computer (such as may be remotely located), and/or another database (such as may be remotely located). Communication between the mobile communications device 440, another mobile communications device (such as may be remotely located), the computer 470, another computer (such as may be remotely located), the database comprising the image data received from the mobile communications device 440, and/or another database (such as may be remotely located) may be via one or more of the Internet, a cellular network, a satellite communications network, a local area network, a wireless network, a Wi-Fi connection, other wireless connections (e.g., BLUETOOTH), an Ethernet connection, a digital subscriber line ("DSL"), a telephone line, coaxial cable, and/or other means.

The image data in the database may be anonymous with respect to identification of any patient corresponding to any portion of the image data. The image data may further comprise pathology information associated with each response.

Figure 7:
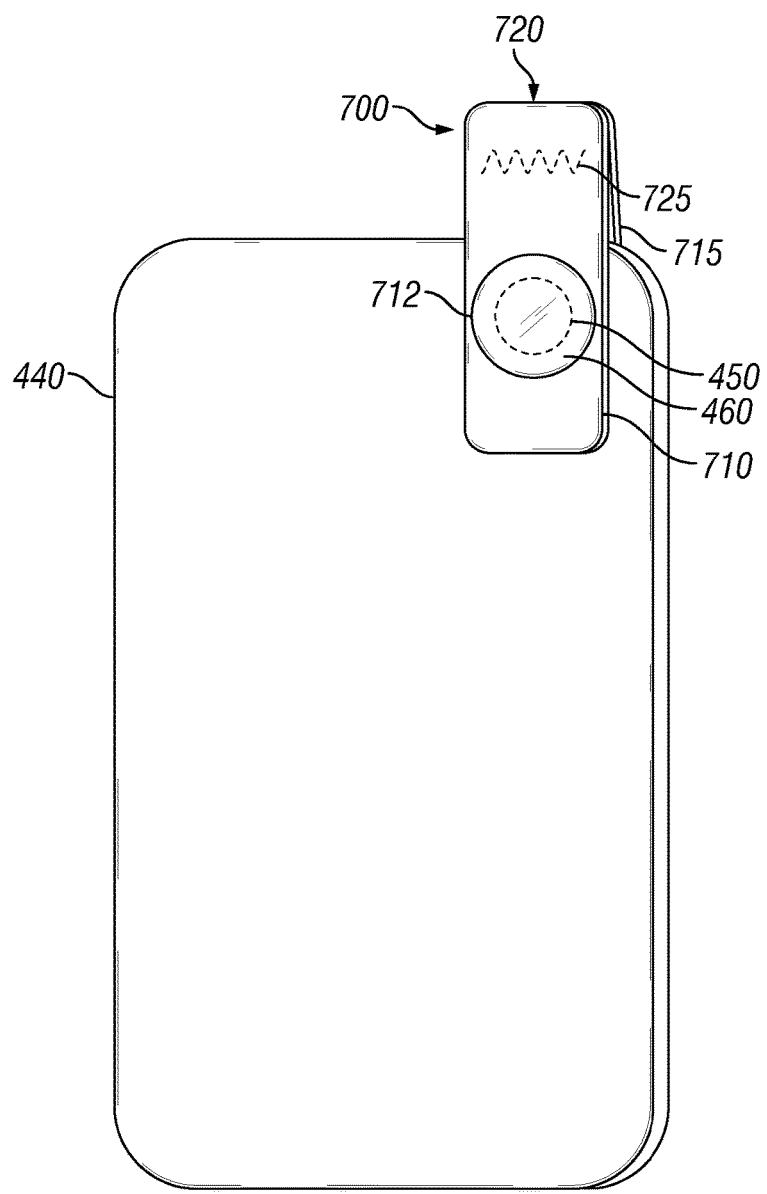
FIG. 7 is a schematic view of at least a portion of apparatus according to one or more aspects of the present disclosure.

FIG. 7 is a schematic view of at least a portion of apparatus according to one or more aspects of the present disclosure. FIG. 7 depicts an apparatus 700 comprising the optical component 460 and is operable to hold the optical component 460 in alignment with the camera 450 of the mobile communications device 440. The apparatus 700 may comprise a filter structure 710, a contact structure 715, and an attachment structure 720. The filter structure 710 may comprise an opening 712, and the optical component 460 may be affixed within and/or otherwise held in the opening 712.

At least a portion of one or more of the filter structure 710, the contact structure 715, and the attachment structure 720 is operable to contact the mobile communications device 440. That is, the attachment structure 720 connects the filter structure 710 with the contact structure 715 in a manner operable to attach the apparatus 700 to the mobile communications device 440 and align the optical component 460 with the camera 450. For example, the attachment structure 720 may be or comprise a spring 725 operable to bias the filter structure 710 and the contact structure 715 into engagement with opposing surfaces (e.g., front and back surfaces) of the mobile communications device 460, such as by an elastic clamping and/or other type of force. However, although other arrangements are also within the scope of the present disclosure.

Figure 8:
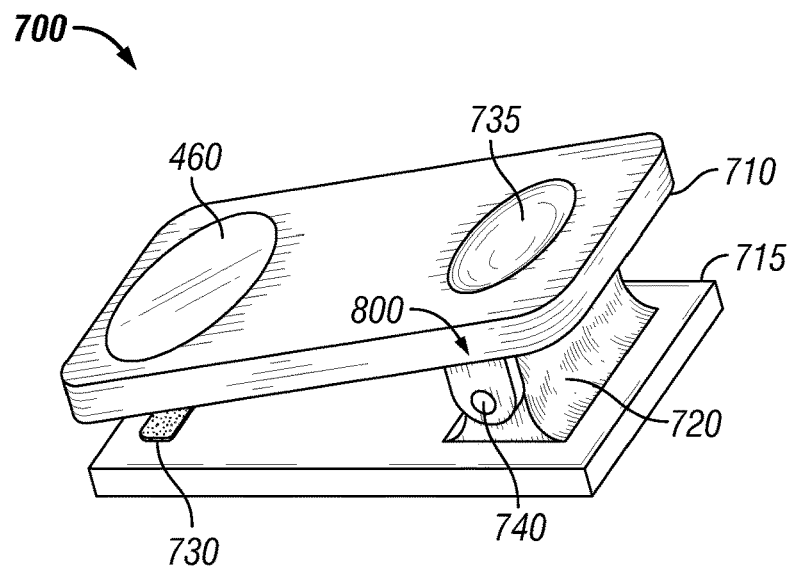
FIG. 8 is a schematic view of at least a portion of apparatus according to one or more aspects of the present disclosure.

FIG. 8 is a perspective view of the apparatus 700 shown in FIG. 7 demonstrating additional, perhaps optional features that may or may not also be depicted in FIG. 7. For example, at least a portion of the filter structure 710 and/or the contact structure 715 may comprise a gripping material 730 that provides substantial gripping force, such as rubber and/or other pliable materials, which may aid in increasing friction between the apparatus 700 and the mobile communications device 440 and aligning the optical component 460 with the camera 450.

The filter structure 710 and/or the contact structure 715 may also comprise one or more finger grooves, recesses, and/or other features 735 that may aid in gripping. The attachment structure 720 may also comprise a pivot 740 and/or otherwise be operable to allow leverage and/or a pinching force to be applied and temporarily separate ends of the filter structure 710 and the contact structure 715, thus allowing insertion of the mobile communications device 440 and alignment of the optical component 460 with the camera 450.

Figure 9:
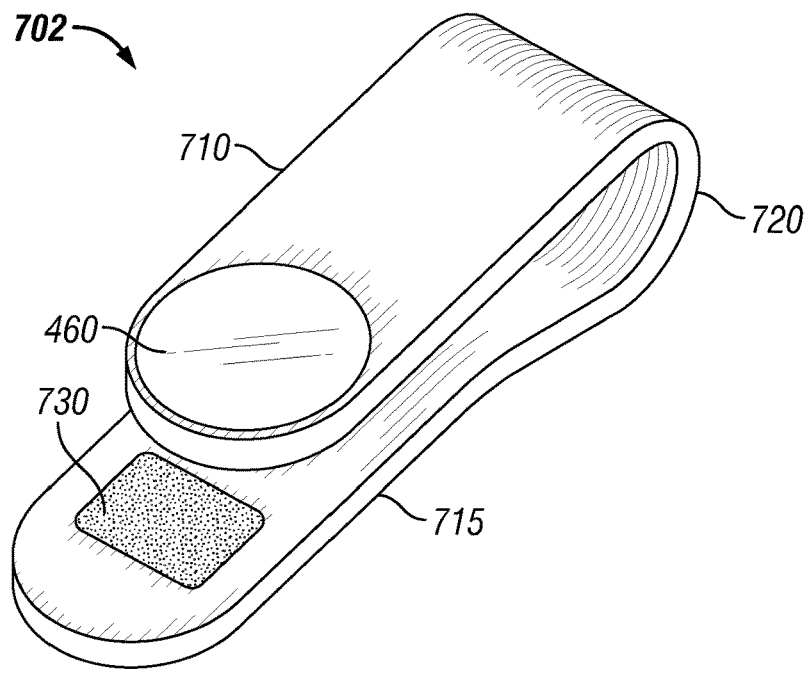
FIG. 9 is a schematic view of at least a portion of apparatus according to one or more aspects of the present disclosure.

FIG. 9 is a perspective view of another implementation of the apparatus 700 shown in FIGS. 7 and 8, designated herein by reference number 702. The apparatus 702 comprises a substantially continuous length of tempered metal and/or other elastic material that has been folded back on itself, thus forming the filter structure 710, the contact structure 715, and the attachment structure 720. The filter structure 710 may be a substantially planar length of the substantially continuous length of tempered metal and/or other elastic material, and comprises the optical component 460. The filter structure 710 may also comprise a portion of the gripping material (as described above) on an interior surface (not shown, but facing the contact structure 715) and/or other features that may be operable to aid in gripping the mobile communications device 440. The contact structure 715 may include one or more arcuate portions of the substantially continuous length of tempered metal and/or other elastic material, collectively extending in a general direction that may be substantially parallel to the filter structure 710, whether before or after assembly to the mobile communications device 440. The contact structure 715 may also comprise a portion of the gripping material 730 described above. The attachment structure 720 may be a curved portion of the substantially continuous length of tempered metal and/or other elastic material, such as may be operable to urge the filter structure 710 and the contact structure 715 towards each other, perhaps in a manner similar to the operation and/or effect of the spring 725 and/or pivot 740 described above.

Figure 10:
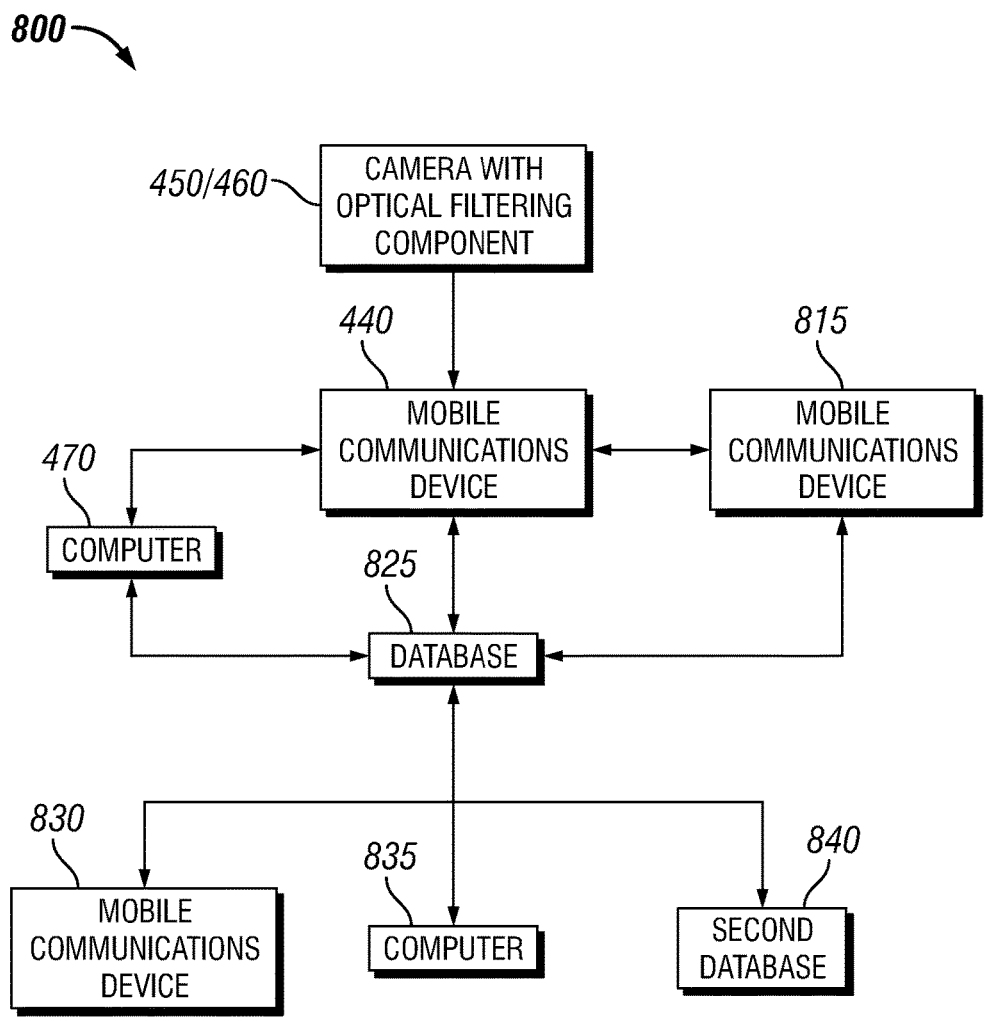
FIG. 10 is a block diagram view of at least a portion of apparatus according to one or more aspects of the present disclosure.

FIG. 10 is a block diagram of at least a portion of a system 800 according to one or more aspects of the present disclosure. FIG. 10 depicts an example implementation of the flow of image data spectrally filtered by the optical component 460 and captured by the camera 450 of the mobile communications device 440. Thus, the system 800 may comprise or otherwise operate in conjunction with the mobile communications device 440.

Referring to FIGS. 4 and 10, collectively, image data may be comprised of one or more images of a human oral cavity of a patient 420 taken using the camera 450 with the optical component 460. The image data may thus be received and/or stored by the mobile communications device 440. The image data may further comprise or be associated with pathology information, such as visual and/or textual information that may be associated with the oral cavity images. The image data may also comprise or be associated with a patient 420 corresponding to the oral cavity images, such as visual and/or textual information associated with the patient 420, such as a photo of the patient's face and text identifying the patient 420. However, the image data may also be managed in a manner intending to preserve the anonymity of the patient 420.

The mobile communications device 440 may be operable to transmit image data to the computer 470, another mobile communications device 815, and/or a database 825. The computer 470 may be operable to receive, store, and transmit image data. The database 825 may be as described above, operable to receive, store, allow access to, and transmit image data. The database 825 may receive image data from the mobile communications device 440, and may otherwise be operable to be accessed by at least one of the mobile communications device 440, the computer 470, and another database 840. The database 825 may also or instead receive image data from the computer 470 after the computer 470 has received image data from the mobile communication device 440. The database 825 may also be operable to transmit image data to at least one of the mobile communications device 440, the computer 470, and the additional database 840.

The database 825 may also be protected using one or more usernames and one or more passwords, such as where each password may grant access to the database 825 for a corresponding username. A user may use such username and password to access the database 825 and may access image data for a patient 420 stored in the database 825. Medical personnel 410 may access image data regarding a specific patient 420 via the database 825.

One or more components of the system 800 may further comprise a mobile communications program operable to allow the mobile communications device 440 to transmit, access, and receive image data utilizing the database 520. Such program may be stored in a memory and/or another non-transitory, computer-readable medium, and may include computer-readable instructions executable for capturing the image data with the mobile communications device 440, storing the image data in a memory of the mobile communications device 440, and transmitting image data from the mobile communications device 440, such as to the computer 470, the database 825, and/or another mobile communications device 815. The program may also include computer-readable instructions executable for accessing the database 825 and/or transmitting, from the database 825 to the mobile communications device 440, data not previously captured by the mobile communications device 440, perhaps including data previously captured by the additional mobile communications device 815.

Figure 11:
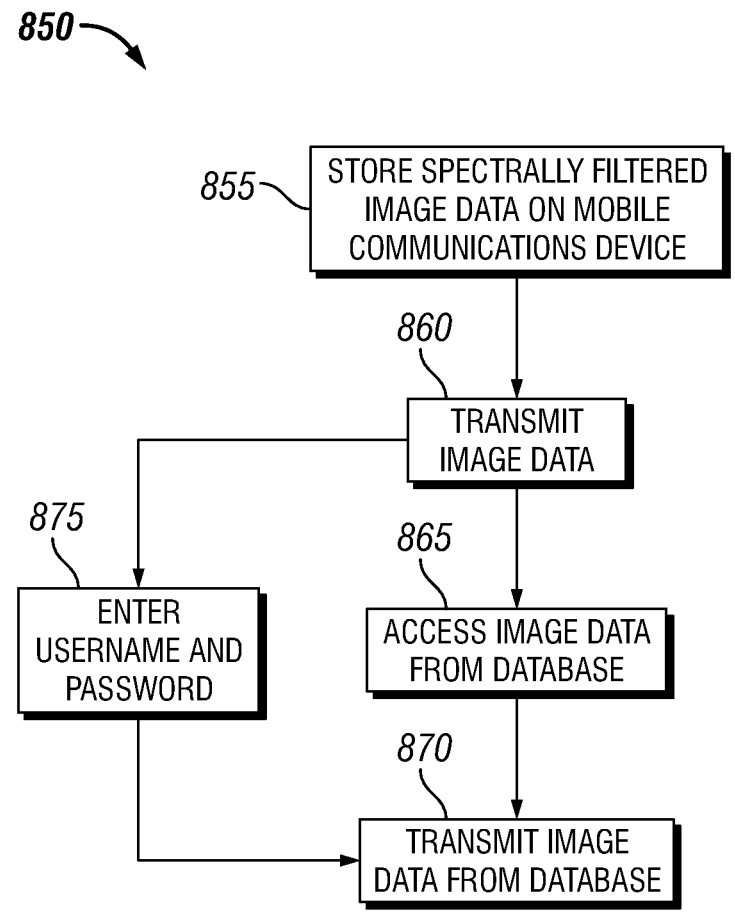
FIG. 11 is a flow-chart diagram of at least a portion of a system according to one or more aspects of the present disclosure.

FIG. 11 is a flow-chart diagram of at least a portion of an example implementation of such a computer program 850 according to one or more aspects of the present disclosure. Referring to FIGS. 4, 10, and 11, collectively, the mobile communications program 850 includes computer-readable instructions executable to store (855) spectrally filtered image data on the mobile communications device 440 and transmit (860) image data from the mobile communications device 440, such as to the computer 470, the database 825, and/or an additional mobile communications device 815. The program 850 may also include computer-readable instructions executable to access (865) image data from the database 825, among other data locations, and transmit (870) image data from the database 825 to the mobile communications device 440. The program 850 may also or instead comprise computer-readable instructions executable to allow a username and/or password to be entered (875) prior to allowing access (865) to and/or transmission (870) of image data from the database 825.

Figure 12:
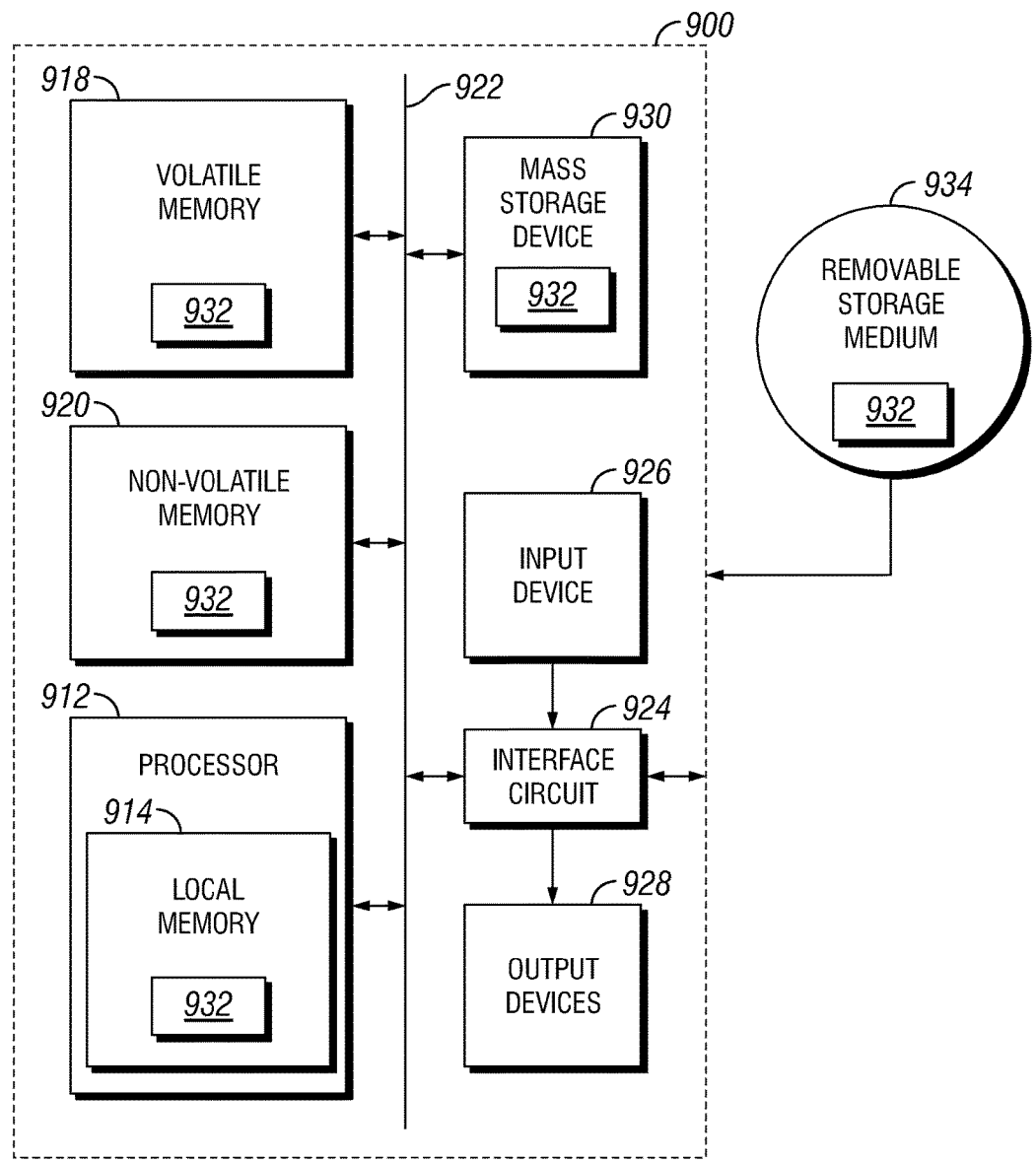
FIG. 12 is a block diagram of at least a portion of a processing system according to one or more aspects of the present disclosure.

FIG. 12 is a schematic view of at least a portion of apparatus according to one or more aspects of the present disclosure. The apparatus comprises a processing system 900 that may execute example machine-readable instructions used to implement one or more of the methods and/or processes described herein, and/or to implement a portion of apparatus described herein. The processing system 900 may be or comprise, for example, one or more processors, controllers, special-purpose computing devices, servers, personal computers, personal digital assistant ("PDA") devices, smartphones, internet appliances, and/or other types of computing devices. The processing system 900 may be implemented within one or more of the mobile communications devices shown in one or more of FIGS. 4, 7, and 10, one or more of the computers shown in one or more of FIGS. 4 and 10, and/or one or more of the databases described above with respect to FIG. 4 and/or shown in FIG. 10, perhaps including a combination thereof. Components of the processing system 900 may be utilized in the execution of the method 600 shown in FIG. 6, the method 850 shown in FIG. 11, and/or other methods and/or processes within the scope of the present disclosure.

The processing system 900 comprises a processor 912 such as, for example, a general-purpose programmable processor. The processor 912 comprises a local memory 914, and executes coded instructions 932 present in the local memory 914 and/or in another memory device. The processor 912 may execute, among other things, machine-readable instructions or programs to implement the methods and/or processes described herein. The programs stored in the local memory 914 may include program instructions or computer program code that, when executed by an associated processor, enable apparatus described herein and/or otherwise to perform tasks as described herein and/or otherwise. The processor 912 may be, comprise, or be implemented by one or more processors of various types suitable to the local application environment, and may include one or more of general-purpose computers, special purpose computers, microprocessors, digital signal processors ("DSPs"), field-programmable gate arrays ("FPGAs"), application-specific integrated circuits ("ASICs"), and processors based on a multi-core processor architecture, as non-limiting examples. Of course, other processors from other families are also appropriate.

The processor 912 is in communication with a main memory including a volatile memory 918 and a non-volatile memory 920 via a bus 922. The volatile memory 918 may be, comprise, or be implemented by random access memory (RAM), static random access memory (SRAM), synchronous dynamic random access memory (SDRAM), dynamic random access memory (DRAM), RAMBUS dynamic random access memory (RDRAM) and/or other types of random access memory devices. The non-volatile memory 920 may be, comprise, or be implemented by read only memory, flash memory and/or other types of memory devices. One or more memory controllers (not shown) may control access to the volatile memory 918 and/or the non-volatile memory 920.

The processing system 900 also comprises an interface circuit 924. The interface circuit 924 may be, comprise, or be implemented by various types of standard interfaces, such as an Ethernet interface, a universal serial bus (USB), a third generation input/output (3GIO) interface, a wireless interface, and/or a cellular interface, among others. The interface circuit 924 may also comprise a graphics driver card. The interface circuit 924 may also comprise a communication device such as a modem or network interface card to facilitate exchange of data with external computers via a network (e.g., Ethernet connection, digital subscriber line ("DSL"), telephone line, coaxial cable, cellular telephone system, satellite, etc.).

One or more input devices 926 may be connected to the interface circuit 924. The input device(s) 926 permit a user to enter data and commands into the processor 912. The input device(s) 926 may be, comprise, or be implemented by, for example, a keyboard, a mouse, a touchscreen, a track-pad, a trackball, an isopoint, and/or a voice recognition system, among others.

One or more output devices 928 may be connected to the interface circuit 924. The output devices 928 may be, comprise, or be implemented by, for example, display devices (e.g., a liquid crystal display or cathode ray tube display (CRT), among others), printers, and/or speakers, among others.

The processing system 900 may also comprise one or more mass storage devices 930 for storing machine-readable instructions and data. Examples of such mass storage devices 930 comprise floppy disk drives, hard drive disks, compact disk (CD) drives, and digital versatile disk (DVD) drives, among others. The coded instructions 932 may be stored in the mass storage device 930, the volatile memory 918, the non-volatile memory 920, the local memory 914, and/or a removable storage medium 934, such as a CD or DVD. Thus, the modules of the processing system 900 may be implemented in accordance with hardware (embodied in one or more chips including an integrated circuit such as an application specific integrated circuit), or may be implemented as software or firmware for execution by a processor. In particular, in the case of firmware or software, the embodiment can be provided as a computer program product including a computer-readable medium or storage structure embodying computer program code (i.e., software or firmware) thereon for execution by the processor.

In view of the entirety of the present disclosure, including FIGS. 1-12, a person having ordinary skill in the art should readily recognize that the present disclosure introduces an apparatus comprising an optical component operable to spectrally filter images taken by a mobile communications device.

The optical component may comprise at least one of a low-pass filter, a high-pass filter, a band-stop filter, and/or a band-pass filter.

The apparatus may further comprise a filter structure comprising an opening, a contact structure, and an attachment structure. The optical component may be held in the opening. The attachment structure may connect the contact structure to the filter structure, and may be operable to attach the apparatus to the mobile communications device. At least a portion of one of the filter structure, the contact structure, and the attachment structure may contact the mobile communications device.

The attachment structure may comprise a curved portion.

The attachment structure may comprise a spring.

At least one of the filter structure, attachment structure, and contact structure may comprise one or more finger grooves, patterned portions, and/or additional openings.

At least a portion of one of the filter structure, attachment structure, and contact structure may comprise a gripping material.

At least a portion of one of the filter structure, attachment structure, and contact structure may comprise a textured material.

At least a portion of the filter structure, attachment structure, and contact structure may comprise a leverage portion, wherein the leverage is operable to allow leverage to be applied to one or more portions of the apparatus.

The present disclosure also introduces a system comprising a mobile communications device, wherein the mobile communications device comprises a camera and is operable to receive, store, and transmit image data originating from the camera; an optical component operable to spectrally filter images entering the camera; and a database operable to receive, store, allow access to, and transmit image data, wherein image data comprises one or more images of a human oral cavity taken using the camera and optical component.

The system may further comprise a filter attachment operable to hold the optical component in alignment with the camera.

The system may further comprise an illumination source operable to produce light with wavelength of about 450 nm or otherwise ranging from about 350 nm to about 500 nm and an intensity that may be about 500 mW or otherwise in the range of about 75 mW to about 2000 mW.

The system may further comprise one or more eyewear devices comprising at least one of a high-pass, low-pass filter, a band-stop filter, and/or a band-pass filter.

The mobile communications device may be operable to transmit image data to at least one of a second mobile communications device, a computer, and the database.

The system may further comprise a computer operable to receive image data, store image data, and transmit image data.

The database may be protected using one or more user names and/or passwords, which may grant access to the database for a username.

The database may be operable to be accessed by at least one of the mobile communications device, the computer, and a second database.

The database may be operable to transmit image data to at least one of the mobile communications device, the computer, and the second database.

A user may access image data for a patient stored on the database.

The database may allow access to image data, which may be anonymous.

The image data and/or database may further comprise pathology information associated with a patient.

The system may further comprise a mobile communications program operable to allow a mobile communications device to transmit, access, and receive image data utilizing the database.

The present disclosure also introduces a mobile communications program comprising a set of computer readable instructions to store image data on a mobile communications device and transmit image data from the mobile communications device. The image data may comprise spectrally filtered images.

The image data and/or database may further comprise pathology information.

The computer readable instructions may further comprise instructions to access image data from a database and transmit image data from the database to the mobile communications device.

The database may be protected using one or more usernames and one or more passwords, wherein each password may grant access to the database for a user.

The user may be able to access image data stored on the database from a patient.

The program may access image data anonymously from the database.

The present disclosure also introduces an apparatus comprising: a filter structure; an optical component carried by the filter structure and operable to spectrally filter an image being taken by a camera of a mobile communications device; a contact structure; and an attachment structure connecting the contact structure to the filter structure and operable to attach the optical component to the mobile communications device and align the optical component with the camera.

The filter structure may comprise an opening in which the optical component is positionally fixed.

The optical component may comprise at least one of a low-pass filter, a high-pass filter, a band-stop filter, and/or a band-pass filter.

The attachment structure may elastically urge the optical component towards the camera.

The attachment structure may comprise a spring urging the filter structure and the contact structure towards each other.

The present disclosure also introduces a system comprising: an illumination source operable to direct light having a predetermined wavelength and intensity into a human oral cavity; a mobile communications device comprising a camera and operable to obtain, store, and transmit image data obtained utilizing the camera, wherein the image data is dependent upon: a response of tissue in the human oral cavity to the produced light; and an optical component aligned with the camera and operable to spectrally filter the response; an attachment structure coupled to the mobile communications device, wherein the attachment structure comprises the optical component and aligns the optical component with the camera; and a database operable to receive and store the image data.

The predetermined wavelength may range between about 350 nm and about 500 nm, and the predetermined intensity may range between about 75 mW and about 2000 mW. The predetermined wavelength may be about 450 nm, and the predetermined intensity may be about 500 mW.

The system may further comprise eyewear, wherein the eyewear comprises at least one of a high-pass filter, a low-pass filter, a band-stop filter, and/or a band-pass filter.

The illumination source may comprise a first type of filter, and the optical component may comprise a second type of filter. The first and second types of filters may be different ones selected from the group consisting of a low-pass filter, a high-pass filter, a band-stop filter, and/or a band-pass filter. The system may further comprise eyewear comprising the second type of filter.

The mobile communications device may be operable to transmit the image data to at least one of: another mobile communications device; a computer; and the database.

The system may further comprise a computer separate from the mobile communications device and the database, wherein the computer is operable to: receive the image data; store the image data; and transmit the image data. The database may be operable to be accessed by, and transmit the image data to: the mobile communications device; the computer; and another database.

The image data in the database may be anonymous with respect to identification of any patient corresponding to any portion of the image data.

The image data may further comprise pathology information associated with each response.

The system may further comprise eyewear and a computer separate from the mobile communications device and the database, wherein: the predetermined wavelength ranges between about 350 nm and about 500 nm; the predetermined intensity ranges between about 75 mW and about 2000 mW; the mobile communications device is operable to transmit the image data to another mobile communications device, the computer, and the database; the computer is operable to receive, store, and transmit the image data; the image data in the database is anonymous with respect to identification of any patient corresponding to any portion of the image data; the image data further comprises pathology information associated with each response; the database is operable to be accessed by, and transmit the image data to, the mobile communications device, the computer, and another database; the illumination source comprises a first type of filter; the optical component comprises a second type of filter; the first and second types of filters may be different ones selected from the group consisting of a low-pass filter, a high-pass filter, a band-stop filter, and/or a band-pass filter; and the eyewear comprises the second type of filter.

The present disclosure also introduces a mobile communications program product comprising: a non-transitory, computer-readable medium; and computer-readable instructions stored on the medium and executable for: capturing spectrally filtered images with a camera of a mobile communications device having a discrete optical filter attached to but not manufactured with the mobile communications device; storing the spectrally filtered images in a memory of the mobile communications device; and transmitting data associated with the spectrally filtered images from the mobile communications device.

The computer-readable instructions may be further executable for receiving, storing, and transmitting pathology information related to each image.

The computer-readable instructions may be further executable for: accessing a database comprising data not captured by the mobile communications device; and transmitting, from the database to the mobile communications device, data not previously captured by the mobile communications device.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

The Abstract at the end of this disclosure is provided to comply with 37 C.F.R. § 1.72(b) to allow the reader to quickly ascertain the nature of the technical disclosure. It is submitted with the understanding that it will not be used to interpret or limit the scope or meaning of the claims.

What is claimed is:

1. An oral cavity (pre-)cancer and/or mucosal abnormality screening apparatus comprising:
    an optical apparatus comprising a first optical component and operable to hold the first optical component in alignment with a camera of a mobile communications device, wherein:
        the optical apparatus comprises:
            a filter structure;
            a contact structure; and
            an attachment structure;
        the filter structure comprises an opening;
        the first optical component is affixed within the opening;
        the first optical component is a low-pass or high-pass filter and is configured to complement a second optical component on an illumination apparatus, the second optical component comprising a high-pass filter corresponding to the low-pass filter of the first optical component or a low pass filter corresponding to the high-pass filter of the first optical component, to enable visual observation of the (pre-)cancer and/or mucosal abnormalities in the oral cavity;
        the filter structure and the contact structure are each operable to contact the mobile communications device, and the attachment structure connects the filter structure with the contact structure in a manner operable to attach the optical apparatus to the mobile communications device and align the first optical component with the camera;
        the attachment structure comprises a spring operable to bias the filter structure and the contact structure into engagement with opposing front and back surfaces of the mobile communications device by an elastic clamping force;
        the filter structure and the contact structure each comprise a rubber gripping material increasing friction between the optical apparatus and the mobile communications device and aligning the first optical component with the camera;
        the filter structure and the contact structure each comprise one or more finger grooves, recesses, and/or other features that aid in gripping by a human hand; and
        the attachment structure comprises a pivot operable to allow leverage and/or a pinching force to temporarily separate ends of the filter structure and the contact structure, thus allowing insertion of the mobile communications device and alignment of the first optical component with the camera,
    wherein the first and second complementary optical components are collectively configured to filter substantially all visible light emitted by the illumination apparatus, including that which reflects off of surfaces of the oral cavity, such that only light resulting from fluorescence emanating from the (pre-)cancer and/or mucosal abnormalities in the oral cavity.

2. The oral cavity (pre-)cancer and/or mucosal abnormality screening apparatus of claim 1 further comprising:
    the illumination apparatus comprising a housing, a first end cap, an interstitial member, and a second end cap, wherein:
        the first end cap, the housing, the interstitial member, and the second end cap are coupled end-to-end in the order listed;
        the housing is or comprises a partially or substantially cylindrical tube;
        one or more recessed and/or protruding features formed integrally with or otherwise coupled to the housing extend along at least a portion of the housing to assist with securely gripping the illumination apparatus;
        the housing comprises external threads coupling with the first end cap;
        the housing comprises internal threads coupling with the interstitial member;
        the housing comprises substantially rigid materials able to be disinfected and sterilized for use in a dental office;
        the housing contains an electrical energy source comprises a battery;
        the first end cap comprises a control operable to electrically connect the electrical energy source to other electronic components of the illumination apparatus;
        the first end cap comprises one or more patterned, recessed, and/or protruding portions that assist in removing and/or assembling the first end cap to the housing;
        the interstitial member comprises a light source selectively energized by the electrical energy source via operation of the control;
        the light source comprises a light emitting diode (LED) that emits in the blue and/or violet sections of the visible spectrum at an intensity from about 75 mW to about 2000 mW;
        the interstitial member comprises one or more components forming an electrical path between the electrical energy source and the light source;
        the second end cap comprises the second optical component that is in substantial optical alignment with the light source and light emitted therefrom;
        an O-ring is positioned between the second optical component and an inside lip of the second end cap to create a seal preventing fluid from entering the illumination apparatus between the second optical component and the inside lip;
        the second end cap comprises a diffuser positioned to diffuse the light emitted by the light source before the light is incident upon the second optical component to reduce sharpness of edges of a beam of the light emitted by the light source;
        a reflector is positioned at least partially within the second end cap in substantial optical alignment between the light source and the second optical component;
        an internal surface of the reflector centrally focuses the light emitted by the light source;
        the reflector is secured within the second end cap by a retaining ring;
        the retaining ring has an internal sloped surface cooperative with an external sloped surface of the reflector, such that assembling the retaining ring into corresponding features of the second end cap urges the sloped surfaces together, thus urging the reflector towards the internal lip of the second end cap and compressing the O-ring to form a seal;

the cooperating sloped surfaces also center the reflector relative to a longitudinal axis of the second end cap to optically align the reflector between the light source and the second optical component;

a portion of the external surface of the interstitial member comprises one or more flats aiding in preventing the apparatus from rolling when resting on a substantially horizontal surface;

at least a portion of an exterior surface of one or more of the housing, the first end cap, the interstitial member, and the second end cap comprises a rubber material that aids in gripping by a human hand;

the O-ring is a first O-ring, and compression of a second O-ring provides a sealed interface between the second end cap and the interstitial member;

compression of a third O-ring provides a sealed interface between the interstitial member and the housing; and compression of a fourth O-ring provides a sealed interface between the housing and the first end cap.

3. The oral cavity (pre-)cancer and/or mucosal abnormality screening apparatus of claim 2 wherein:

a medical person utilizes the optical apparatus and the illumination apparatus to perform oral examination of a patient to identify oral cancer, pre-cancer, and/or other oral mucosal abnormalities.

4. The oral cavity (pre-)cancer and/or mucosal abnormality screening apparatus of claim 3 wherein the first and second optical components collectively filter out substantially all visible light emitted by the illumination source, including that which reflects off of surfaces of the oral cavity of the patient, such that only a fluorescent signal from the tissue is transmitted to the camera.

5. The oral cavity (pre-)cancer and/or mucosal abnormality screening apparatus of claim 2 further comprising:

a container; and an insert positioned within the container and having recessed features each individually sized to receive a corresponding one of the optical apparatus and the illumination apparatus.

6. The oral cavity (pre-)cancer and/or mucosal abnormality screening apparatus of claim 3 wherein:

an eyewear device is worn by the medical personnel during the oral examination; and the eyewear device comprises a third optical component having substantially identical filtering properties to the first optical component and utilized in conjunction with the second optical component, in that:

lenses of the eyewear device each comprise a filter of the same type as the filter of the first optical component, such that the filters of the first and third optical components filter light substantially identically, such that only the light resulting from fluorescence of the mucosal abnormalities is transmitted to the camera and remains substantially visible the medical personnel wearing the eyewear device, and such that at least a portion of the fluorescence transmitted to the camera is substantially identical to at least a portion of the fluorescence visible to the medical personnel wearing the eyewear device; and the combination of the low-pass and high-filters is operable in conjunction with the light emitted by the illumination apparatus to identify the (pre-)cancer and/or mucosal abnormalities in the oral cavity of the patient.

7. The oral cavity (pre-)cancer and/or mucosal abnormality screening apparatus of claim 6 further comprising:

a container; and an insert positioned within the container and having recessed features each individually sized to receive a corresponding one of the optical apparatus, the illumination apparatus, and the eyewear device.

8. The oral cavity (pre-)cancer and/or mucosal abnormality screening apparatus of claim 1 further comprising a computer operable to:

receive spectrally filtered image data from the mobile communications device; and store the image data.

9. The oral cavity (pre-)cancer and/or mucosal abnormality screening apparatus of claim 8 wherein the computer is operable to transmit the image data to another computing device.

10. The oral cavity (pre-)cancer and/or mucosal abnormality screening apparatus of claim 8 wherein the mobile communications device is operable to obtain, store, and transmit image data obtained utilizing the camera, including to transmit the image data to at least one of another mobile communications device, the computer, and a database.

11. The oral cavity (pre-)cancer and/or mucosal abnormality screening apparatus of claim 10 wherein the database is:

embodied or implemented in the computer or another computing device; and operable to be accessed by the mobile communications device, another mobile communications device, the computer, another computer, and/or another database.

12. The oral cavity (pre-)cancer and/or mucosal abnormality screening apparatus of claim 11 wherein the database is operable to transmit at least a portion of the image data to the mobile communications device, another mobile communications device, the computer, another computer, and/or another database.

13. The oral cavity (pre-)cancer and/or mucosal abnormality screening apparatus of claim 10 wherein the database is anonymous with respect to identification of any patient corresponding to any portion of the image data.

14. The oral cavity (pre-)cancer and/or mucosal abnormality screening apparatus of claim 10 wherein the database is protected via one or more usernames and one or more passwords, each password granting access to the database for a corresponding username.

15. The oral cavity (pre-)cancer and/or mucosal abnormality screening apparatus of claim 8 wherein the image data further comprises pathology information associated with abnormalities indicated by the image data.

16. The oral cavity (pre-)cancer and/or mucosal abnormality screening apparatus of claim 8 wherein the image data:

is comprised of one or more images of a human oral cavity of a patient taken using the camera with the first optical component;

is received and/or stored by the mobile communications device;

comprises pathology information, including visual and/or textual information associated with oral cavity images encoded in the image data; and comprises identification information associated with a patient corresponding to the oral cavity images, including visual and/or textual information associated with the patient.

17. The oral cavity (pre-)cancer and/or mucosal abnormality screening apparatus of claim 16 wherein the identification information associated with the patient includes a photo of the patient's face and text identifying the patient.

18. The oral cavity (pre-)cancer and/or mucosal abnormality screening apparatus of claim 1 further comprising a mobile communications program operable to allow the mobile communications device to transmit, access, and receive image data utilizing the database.

19. The oral cavity (pre-)cancer and/or mucosal abnormality screening apparatus of claim 18 wherein the program is stored in a memory and/or another non-transitory, computer-readable medium, and includes computer-readable instructions executable for:
- capturing the image data with the mobile communications device;
- storing the image data in a memory of the mobile communications device; and
- transmitting image data from the mobile communications device to the computer, the database, and/or another mobile communications device.

20. The oral cavity (pre-)cancer and/or mucosal abnormality screening apparatus of claim 19 wherein the program also includes computer-readable instructions executable for accessing the database and/or transmitting, from the database to the mobile communications device, data not previously captured by the mobile communications device.

* * * * *